(12) United States Patent
Sümegi et al.

(10) Patent No.: US 7,994,182 B2
(45) Date of Patent: Aug. 9, 2011

(54) QUINAZOLINONE-DERIVATIVES AND THEIR USE FOR PREPARATION OF PHARMACEUTICAL COMPOSITIONS HAVING PARP ENZYME INHIBITORY EFFECT

(75) Inventors: Balázs Sümegi, Pécs (HU); Kálmán Hideg, Pécs (HU); Tamás Kálai, Pécs (HU)

(73) Assignee: Pecsi Tudomanyegyetem, Pecs (HU)

( * ) Notice: Subject to any disclaimer, the term of this patent is extended or adjusted under 35 U.S.C. 154(b) by 996 days.

(21) Appl. No.: 10/554,749

(22) PCT Filed: Apr. 30, 2004

(86) PCT No.: PCT/HU2004/000044
§ 371 (c)(1),
(2), (4) Date: Jul. 10, 2006

(87) PCT Pub. No.: WO2004/096779
PCT Pub. Date: Nov. 11, 2004

(65) Prior Publication Data
US 2007/0042935 A1    Feb. 22, 2007

(30) Foreign Application Priority Data

Apr. 30, 2003 (HU) .................... 0301173

(51) Int. Cl.
*A61K 31/517* (2006.01)
*C07D 239/88* (2006.01)
*C07D 403/12* (2006.01)

(52) U.S. Cl. ............. 514/266.22; 514/266.3; 544/285; 544/287

(58) Field of Classification Search ............ 514/266.22, 514/266.3; 544/285, 287
See application file for complete search history.

(56) References Cited

U.S. PATENT DOCUMENTS 3,073,826 A    1/1963   Scarborough
4,861,780 A *  8/1989   Takahashi et al. ....... 514/266.21

FOREIGN PATENT DOCUMENTS

| EP | 1396488  | 3/2004 |
| WO | 9911624  | 3/1999 |
| WO | 02/48117 | 6/2002 |

OTHER PUBLICATIONS

Kulcsar, Gyozo et al: "Synthesis and Study of New 4-Quinazolinone Inhibitors of the DNA Repair Enzyme Poly(ADP-Ribose) Polymerase ( PARP )" ARKIVOC (Gainesville, FL, United States), (5), 121-131 Coden: Agfuar URL: HTTP://WWW.ARKAT-USA.ORG/ARK/JOURNAL/2003/ BERNATH/GB-733J/GB- 733J.PDF, Jun. 11, 2003, XP002291367, the whole document.
Hankovszky O H et al: "New Antiarrhithmic Agents. 2,2,5,5-Tetramethyl-3-Pyrroline-3-Carboxa Mides and 2,2,5,5-Tetramethylpyrrolidine-3-Carboxami Des" Journal of Medicinal Chemistry, American Chemical Society. Washington, US, vol. 29, No. 7, 1986, pp. 1138-1152, XP002068557 ISSN: 0022-2623, abstract.
Krishna M C et al: "Studies of Structure-Activity Relationship of Nitroxide Free Radicals and Their Precursors As Modifiers Against Oxidative Damage" Journal of Medicinal Chemistry, American Chemical Society. Washington, US, vol. 41, No. 8, 1998, pp. 3477-3492, XP001146049 ISSN: 0022-2623; abstract.
Griffin R J et al: "Resistance Modifying Agents.5.Synthesis and Biological Properties of Quinazolinone Inhibitors of the DNA Repair Enzyme Poly(ADP-Ribose) Polymerase (PARP)" Journal of Medicinal and Pharmaceutical Chemistry, American Chemical Society. Easton, US, vol. 41, 1998, pp. 5247-5256, XP002208913; abstract.
Manabu Hori et al: "Nootropic Agents, 4-Alkoxy-2-(1-Piperazinyl)Quinazoline Derivatives" Chemical and Pharmaceutical Bulletin, Pharmaceutical Society of Japan. Tokyo, JP, vol. 39, No. 2, Feb. 1991, pp. 367-371, XP002128281 ISSN: 0009-2363.
International Search Report dated Aug. 23, 2004 from PCT/HU2004/000044.
Murav'Eva, K. M. et al: "Derivatives of 2-Mercapto-4-Quinazolone As Compounds Having Potential Antitubercular Activity", retrieved from STN Database accession No. 1969:96748, 1967, pp. 411-414, IZD. "Zinatne". Riga, USSR, XP002291368.

\* cited by examiner

*Primary Examiner* — James O Wilson
*Assistant Examiner* — Tamthom Truong
(74) *Attorney, Agent, or Firm* — Young & Thompson

(57) ABSTRACT

The subject of the present invention are quinazoline derivatives and their pharmaceutically acceptable salts of general formula (I), that inhibit a DNA-repairing enzyme, poly(ADP-ribose) polymerase (PARP), enabling them to be used for the preparation of pharmaceutical compositions for preventing or treating illnesses where PARP-inhibition yields a beneficial effect. In general formula (I) $R^1$ stands for either hydrogen or a group of general formula (a); $R^2$ stands for a) hydrogen or $C_{1-6}$ alkyl group, if $R^1$ is other than hydrogen, and b) if $R^1$ is hydrogen, then $R^2$ may be a group of general formula (b), (c) or (d). The subject of the present invention also embraces the preparation processes of the compounds described above.

9 Claims, 4 Drawing Sheets

(I)

(a)

(b)

(c)

(d)

(e)

(A)

(B)

(1)

(1')

(2)

(3)

(4)

(5)

Reaction Scheme A

Reaction Scheme B

Reaction Scheme C

Reaction Scheme D

Reaction Scheme A'

Reaction Scheme B'

Reaction Scheme C'

Reaction Scheme D'

QUINAZOLINONE-DERIVATIVES AND THEIR USE FOR PREPARATION OF PHARMACEUTICAL COMPOSITIONS HAVING PARP ENZYME INHIBITORY EFFECT

FIELD OF THE INVENTION

The subject of the present invention are quinazolinone derivatives of general formula (I), that inhibit a DNA-repairing enzyme, poly(ADP-ribose) polymerase (PARP), enabling them to be used for the preparation of pharmaceutical compositions for preventing or treating illnesses where PARP-inhibition yields a beneficial effect.

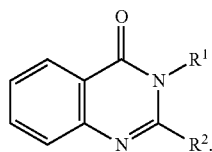

(I)

BACKGROUND OF THE INVENTION

The PARP enzyme occurring in the eukaryotic nucleus is a DNA-binding protein, having a serious role in the genomical repair mechanism.[1,2] The PARP enzyme is activated directly by genotoxic agents (alkylating agents, reactive oxygen radicals, ionising radiation) or indirectly by DNA stand break occuring after the enzymatic excision of a mismatched DNA base. PARP catalyses the biochemical transformation of nicotinamide adenine dinucleotide (NAD) to poly(ADP-ribose) and nicotinamide, hence the latter is one of the weak feedback inhibiting agents of the enzyme. Although PARP plays an important role in the genomical repair, its significant activation entails extensive ADP-ribosylation and the depletion of NAD depots leading to the decrease of the ATP-level due to resynthesising NAD, and finally, in the lack of ATP and NAD it causes failure in the mitochondrial function and ultimately cell death.

The structural formulas of the first PARP inhibitors showed homology to nicotinamide and benzamide analogues.[3] Recent research was aimed at the synthesis of more effective and more selective PARP inhibitors fitted to the crystal structure of PARP's catalytic domain, leading to the discovery of polycyclic amides and lactams.[4,5] Presently, the most effective compound is 8-hydroxy-2-methyl-quinazoline-4(3H)-one [NU-1025, see formula (A), $IC_{50}$=400 nM].[6,7] Later, new tricyclic inhibitors were prepared starting from this compound.

The present inventors have already synthesised a promising antiarrhythmic 4-quinazolinone derivative named H-2641, see formula (B)[8]. After this, its PARP inhibiting activity could be studied and compared to the same of basic quinazolinone compounds of formulae (1)-(3). We note that, according to earlier observations, substitution at position 3 of the quinazolinone ring increased the $IC_{50}$ value of the compounds, so further investigations in this direction did not seem to be promising.[6]

The elaboration of the present invention was aimed at the preparation of new compounds containing the basic quinazoline-4(3H) ring bearing such sidechains in positions 2 or 3 that have an advantageous effect on the pharmacological properties of the molecule primarily by increasing their effect against oxidative stress due to the free radical trapping ability of the sidechains.

The effectiveness against oxidative stress can be an advantageous feature of the PARP inhibitors, because this way they can provide an increased protection against cell destruction caused by antiviral[11] and antitumour drugs. The therapeutic application of antiviral and antitumour compounds unavoidably leads to the release of reactive oxygen free radicals. The in stau nascendi capture of these radicals can moderate the side effects of these drugs more than presently used PARP inhibitors could do.

DETAILED DESCRIPTION OF THE INVENTION

The present invention provides the compounds of general formula (I) and their pharmaceutically acceptable salts,

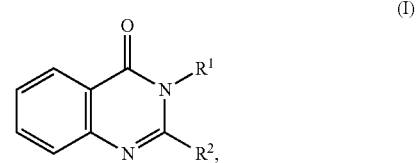

(I)

wherein
R¹ stands for hydrogen or a group of general formula (a)

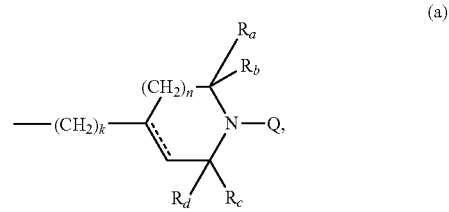

(a)

and
k is 1, 2, 3 or 4,
n is 0 or 1,
Q stands for oxyl group (O.) or hydrogen,
  Ra and Rc independently from each other stand for hydrogen or $C_{1-6}$ alkyl group,
  Rb and Rd independently from each other stand for $C_{1-6}$ alkyl group and the broke line stands for optional valence bond;

$R^2$ stands for a) hydrogen or $C_{1-6}$ alkyl group, if $R^1$ is other than hydrogen, and b) if $R^1$ is a hydrogen, then $R^2$ may stand for (i) a group of general formula (b), wherein the meanings of k, n, Q, Ra, Rb, Rc, Rd and the broken line are as given above,

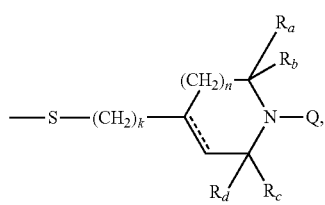
(b)

or (ii) a group of general formula (c), wherein k is 1, 2 or 3; $R^3$ and $R^4$ independently from each other stand for $C_{1-6}$ alkyl group,

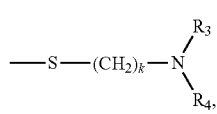
(c)

or together with the attached nitrogen form a group of general formula (e), wherein p is 0 or 1 and R'a, R'b, R'c and R'd independently from each other stand for hydrogen or $C_{1-6}$ alkyl group,

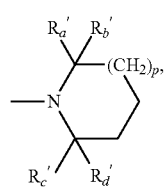
(e)

or (iii) a group of general formula (d), wherein the meanings of n, Q, Ra, Rb, Rc, Rd the broken line are as given above and m is 0, 1, 2 or 3.

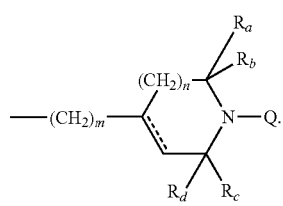
(d)

The advantageous groups of compounds are determined in the subclaims attached.

The following compounds seemed to be extremely advantageous:

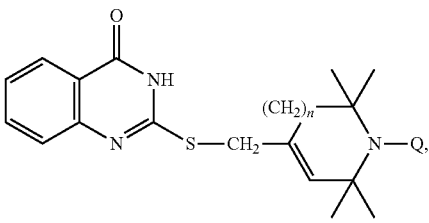

n = 1, Q = H:(15),

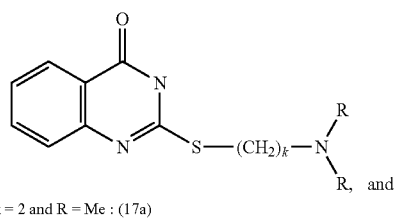

k = 2 and R = Me : (17a)
k = 3 and R = Me : (17b)

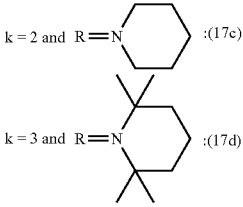 :(17c)

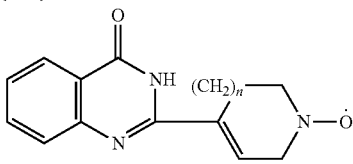 :(17d)

n = 1, and Q = Ȯ : (23)
n = 1, and Q = H : (24)

The compounds (17a) and (17d) proved to be the most advantageous ones.

Compounds of the present invention may contain one or two asymmetrical carbon atoms, when the meanings of the Ra-Rd groups are different. Present invention implicitly involves all the potential isomer forms as well.

The present invention includes also a process for the preparation of compounds of general formula (I) and their pharmaceutically acceptable salts—the meanings of the symbols applied in the formula are given above.

Figure 15:
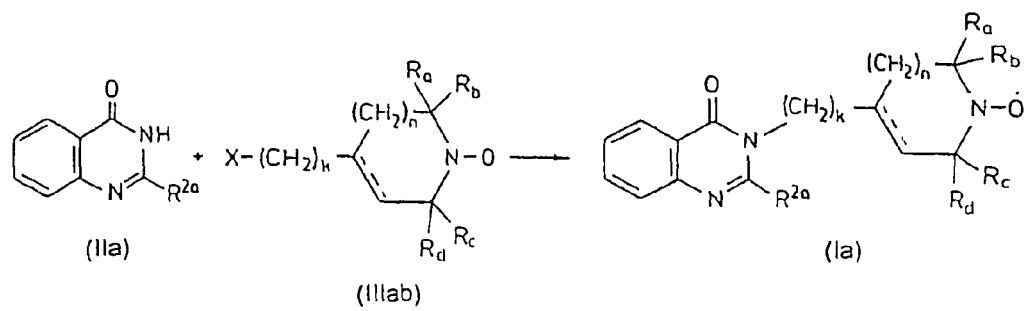
FIG. 15 illustrates Reaction Scheme A.
Figure 16:
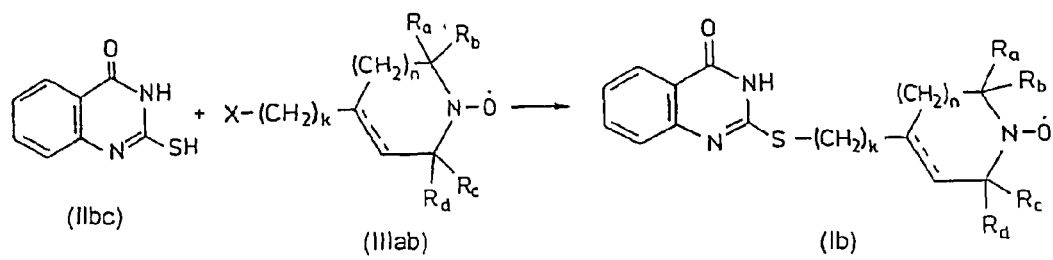
FIG. 16 illustrates Reaction Scheme B.
Figure 17:
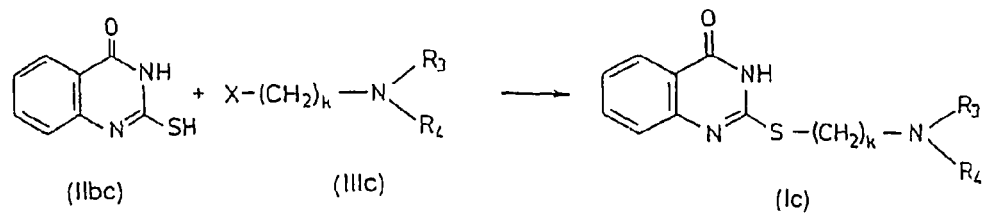
FIG. 17 illustrates Reaction Scheme C.
Figure 18:
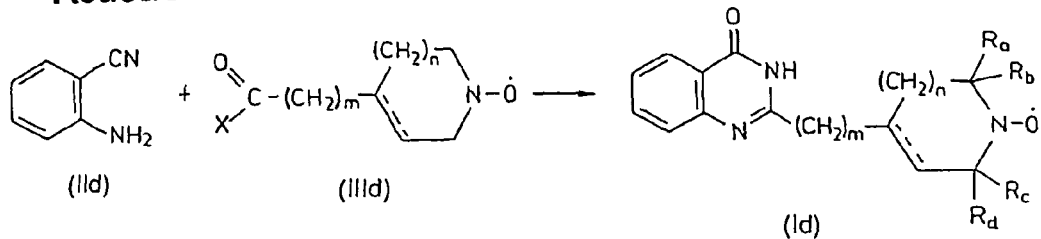
FIG. 18 illustrates Reaction Scheme D.

Referring to FIG. 15, a) in case of the synthesis of compounds of general formula (I) wherein $R^1$ stands for a group of general formula (a), a compound of general formula ($II_a$) is reacted with a compound of general formula ($III_{ab}$)—the meanings of the symbols applied in the formulae are given above, furthermore, in general formula ($II_a$) $R^{2a}$ is either hydrogen or $C_{1-6}$ alkyl group and in general formula ($II_{ab}$) X is a leaving group, preferably a halogen atom, Referring to FIG. 16, b) in case of the synthesis of compounds of general formula (I) wherein $R^2$ stands for a group of general formula (b), a compound of formula ($II_{bc}$) is reacted with a compound of general formula ($III_{ab}$)—the meanings of the symbols applied in formula ($III_{ab}$) are given above, and X is a leaving group, preferably a halogen atom, Referring to FIG. 17, c) in case of the synthesis of compounds of general formula (I) wherein $R^2$ stands for a group of general formula (c), a compound of formula ($II_{bc}$) is reacted with a compound of general formula ($III_c$)—the meanings of the symbols applied in formula ($III_c$) are given above, and X is a leaving group, preferably a halogen, Referring to FIG. 18, d) in case of the synthesis of compounds of general formula (I) wherein $R^2$ stands for a group of general formula (d), a compound of formula ($II_d$) is reacted with a compound of general formula ($III_d$)—the meanings of the symbols applied in formula ($III_d$) are given above, and X is a leaving group, preferably a halogen, The preparation processes of the compounds of present invention are grouped by the side chains to be built in (see, reaction schemes A)-D), FIGS. 15-18). In the examples general synthetic procedures are given for the synthesis of each group of compounds. The synthesis of compounds disclosed in the examples are shown in the reaction schemes A')-D' (see, FIGS. 19-22). Optionally, the oxyl group of compounds prepared according to reaction schemes A), B), and D) can be reduced to hydrogen using known methods. (This transformation is shown in general example V.)

Here we mention that in the reactions shown in schemes A)-D) the presence of such a starting compound is compulsory, that contains a leaving group marked by X. This can be a halogen atom, preferably bromine or chlorine, or a group of general formula—$OSO_2R$, where R stands for e.g. methyl-ethyl- or 4-methyl-phenyl group. Of course, other usual protecting groups can be utilised (See for example T. W. Greene, P. G. M. Wuts: Protective Groups in Organic Synthesis, $3^{rd}$ edition, Hardcover 1999.)

From the compounds of the present invention salts can be formed by known methods. Pharmaceutically acceptable salts are obviously preferred, e.g. salts formed with hydrochloric acid, maleic acid, and ascorbic acid. If the synthesis provides not the desired salt, then the free compounds can be obtained, or it can be transformed to other type of salt by known procedures.

The optically active compounds of general formula (I) can be prepared from the corresponding optically active starting compounds, or the end product, being in mixture form, can be separated to optically active isomers by the usual resolving procedures.

The present invention also includes the pharmaceutical compositions containing any of the new compounds described above and the use of the compounds for the preparation of drugs having PARP enzyme inhibitor effects.

Pharmaceutical compositions embraced by the present invention preferably contain one or more quinazolinone derivatives of general formula (I) or their pharmaceutically accepted salts in 0.1 to 95% by weight as active ingredients, beside the usual auxiliary ingredients used in pharmaceutical compositions.

The pharmaceutical composition embraced by present invention can occur in either solid or liquid forms, and can be used for peroral parenteral or rectal administrations, or for local treatment.

Solid pharmaceutical compositions for peroral use may be powders, capsules, pills, film-coated pills, microcapsules etc, and they may contain carriers, like gelatin, sorbitol, poly (vinyl-pyrrolidone); filling materials like lactose, glucose, starch, calcium phosphate; excipients, like magnesium stearate, talcum, poly(ethylene-glycol), silicon dioxide; moisturizers, like sodium lauryl sulphate.

Liquid pharmaceutical compositions for peroral use can be solutions, suspensions or emulsions, containing carriers like suspending agents, such as gelatin, carboxymethylcellulose; emulgeators, like sorbitane-monooleate; solvents, like water, oils, glycerol, propylene glycol, ethanol; preservatives, such as methyl or propyl esters of p-hydroxy-benzoic acid Pharmaceutical compositions for parenteral use usually consist of the sterile solution of the active ingredient.

The forms of administration mentioned above along with other forms are well known, see manual: Remington's Pharmaceutical Sciences 18th edition, Mack Publishing Co., Easton, USA, (1990).

Pharmaceutical composition embraced by the present invention is prepared by mixing one or more compounds of general formula (I) or its pharmaceutically accepted salt as active ingredient with one or more excipients, then the mixture is transformed to a pharmaceutical composition by known method. The applicable methods can be obtained from scientific literature for example the above mentioned Remington's Pharmaceutical Sciences manual. Pharmaceutical compositions embraced by the present invention contain mostly one dosage unit. The usual daily dose for adults is 0.1 to 5000 mg of the compound of general formula (I), or from its pharmaceutically acceptable salts, which can be administered in one or more portions. The effective dosage can depend on several factors, it is prescribed and determined by the physician on the base of usual parameters (weight, age, extent and stage of the illness, etc.).

SYNTHETIC EXAMPLES

Materials and Methods

Melting points were determined with a Boetius Micro Melting Point apparatus and are uncorrected. Elemental analyses (C, H, N, S) were performed on Fisons EA 1110 CHNS elemental analyser. The IR spectra were consistent with the assigned structure in each case. Mass spectra were recorded on a VG TRIO-2 instrument in the EI mode. $^1$H NMR spectra were recorded with Varian Unity Inova 400 WB spectrometer; chemical shifts were referenced to TMS. Flash column chromatography was performed on Merck Kieselgel 60 (0.040-0.063 mm). The HPLC analyses were performed on an HP1100 instrument using a Hypersyl BDS-C18 column with UV detection at 250 nm. Qualitative TLC was carried out on commercially available plates (20×20×0.02 cm) coated with Merck Kieselgel $GF_{254}$. Compounds with general formulae (1), (2) and (3), and 2-dimethylamino-1-ethyl-chloride, 3-diethylamino-1-propylchloride, 1-(2-chloroethyl)piperidine and 2-aminobenzonitrile were purchased from Aldrich, the compound H-2641[8] with structural formula (B), and compounds with formula (4)[12], (5)[13], (6)[14], (7)[16], (16a-d)[17], (19)[19] and (20)[19] were prepared according to published procedures.

We note here that the compound of formula (1) and the compound of formula (1') are tautomers, thus the two structural formulas describe the same compound. In the present description the oxo form is used uniformly in all formulas containing this structural unit without any theoretical consideration.

I. General Procedure According to Reaction Scheme A) [the Structure of the Referred Compounds can be Identified in Reaction Scheme A')]

A solution of 2-methylquinazolin-4(3H)one (2) (1.60 g, 10.0 mmol), the corresponding compound of formula (6) or (7) carrying an allyl bromide part (10.0 mmol) and $K_2CO_3$ (1.38 g, 10.0 mmol) in DMF (15 ml) is stirred for 6 hours at 90° C. The solvent is evaporated, the residue is dissolved in $CHCl_3$ (30 ml) and washed with brine (10 ml). The organic phase is separated, dried (MgSO$_4$), filtered, evaporated, then the solid residue is purified by flash column chromatography (hexane/EtOAc).

Example I/1

3-[(1-Oxyl-2,2,5,5-tetramethyl-2,5-dihydro-1H-pyrrol-3-yl)methyl]-2-methylqunazolin-4(3H)-one [Compound of Formula (8)]

Yield: 1.77 g, 57% (yellow substance).
Melting point: 110-112° C.
Calculated composition: C$_{18}$H$_{22}$N$_3$O$_2$: C, 68.97; H, 7.40; N, 13.41.
Found composition: C, 68.71; H, 7.39; N, 13.59.
IR (nujol) ν: 1620, 1585, 1570 cm$^{-1}$.
MS (m/z, %): 312 (M$^+$, 6), 282 (21), 138 (75), 122 (100).

II. General Procedure According to Reaction Scheme B) [the Structure of the Referred Compounds can be Identified in Reaction Scheme B')]

A solution of 2-mercaptoquinazolin-4(3H)one (3) (1.78 g, 10.0 mmol), the corresponding compound of formula (6) or (7) carrying an allyl bromide part (10.0 mmol) and K$_2$CO$_3$ (1.38 g, 10.0 mmol) in DMF (25 ml) is stirred for 6 hours at 90° C. The solvent is evaporated, the residue is dissolved in CHCl$_3$ (30 ml), and washed with brine (10 ml). The organic phase is separated, dried (MgSO$_4$), filtered, evaporated, then the solid residue is purified by flash column chromatography (CHCl$_3$/Et$_2$O).

Example II/1

2-{[(1-Oxyl-2,2,5,5-tetramethyl-2,5-dihydro-1H-pyrrol-3-yl)methyl]thio}quinazolin-4(3H)-one (12)

Yield: 1.91 g (58%).
Melting point: 138-140° C.
Calculated composition: C$_{17}$H$_{20}$N$_3$O$_2$S: C, 61.79; H, 6.11; N, 12.73; S, 9.68.
Found composition: C, 61.92; H, 6.30; N, 12.79; S, 9.60.
IR (nujol) ν: 1675, 1605, 1585, 1560 cm$^{-1}$.
MS (m/z, %): 330 (M$^+$, 5), 300 (20), 178 (54), 122 (100).

Example II/2

2-{[(1-Oxyl-2,2,6,6-tetraethyl-1,2,3,6-tetrahydropyridin-4-yl)methyl]thio}quinazolin-4(3H)-one (14)

Yield: 1.51 g (44%).
Melting point: 79-82° C.
Calculated composition: C$_{18}$H$_{22}$N$_3$O$_2$S: C, 62.76; H, 6.44; N, 12.21; S, 9.29.
Found composition: C, 62.72; H, 6.31; N, 12.34; S, 9.44.
IR (nujol) ν: 1670, 1610, 1585, 1560 cm$^{-1}$.
MS (m/z, %): 344 (M$^+$, 6), 314 (35), 136 (61), 121 (100).

III. General Procedure According to Reaction Scheme C) [the Structure of the Referred Compounds can be Identified in Reaction Scheme C')]

A solution of 2-mercaptoquinazolin-4(3H)-one (3) (1.78 g, 10.0 mmol), the corresponding compound of formula (16a), (16b), (16c) or (16d) carrying an alkyl chloride part (10.0 mmol) and K$_2$CO$_3$ (2.26 g, 10.0 mmol) in DMF (25 ml) is stirred for 6 hours at 90° C. The solvent is evaporated, the solid residue is dissolved in CHCl$_3$ (30 ml), and washed with brine (10 ml). The organic phase is separated, dried (MgSO$_4$), filtered, evaporated, then the solid residue is purified by flash column chromatography (CHCl$_3$/Et$_2$O).

Example III/1

2-{[2-(Diethylamino)ethyl]thio}quinazolin-4(3H)-one (17a)

Yield: 1.29 g (52%).
Melting point: 155-157° C.
Calculated composition: C$_{12}$H$_{15}$N$_3$OS: C, 57.81; H, 6.06; N, 16.85; S, 12.86.
Found composition: C, 57.92; H, 6.11; N, 16.80; S, 12.70.
IR (nujol) ν: 1665, 1630, 1570 cm$^{-1}$.
$^1$H NMR (CDCl$_3$) δ$_H$, 8.17 (1H, d), 7.65 (1H, td), 7.55 (1H, d), 7.35 (1H, t), 3.14 (2H, m), 2.92 (2H, m) and 2.48 (6H, s).
MS (m/z, %): 249 (M$^+$, 2), 234 (16), 162 (44), 71 (100).

Example III/2

2-{[3(Dimethylamino)propyl]thio}quinazolin-4(3H)-one (17b)

Yield: 1.18 g (45%).
Melting point: 93-95° C.
Calculated composition: C$_{13}$H$_{17}$N$_3$OS: C, 59.29; H, 6.51; N, 15.96; S, 12.17.
Found composition: C, 59.70; H, 6.51; N, 16.02; S, 12.02.
IR (nujol) ν: 1665, 1630, 1570 cm$^{-1}$.
$^1$H NMR (CDCl$_3$) δ$_H$, 8.16 (1H, d), 7.65 (1H, t), 7.54 (1H, d), 7.34 (1H, t), 3.23 (2H, t), 2.68 (2H, t), 2.38 (6H, s) and 1.96 (2H, m).
MS (m/z, %): 263 (M$^+$, 1), 205 (2), 85 (100), 58 (65).

Example III/3

2-[(2-Piperidin-1-ylethyl)thio]quinazolin-4(3H)-one (17c)

Yield: 2.02 g (70%).
Melting point: 131-133° C.
Calculated composition: C$_{15}$H$_{19}$N$_3$OS: C, 62.26; H, 6.62; N, 14.53; S, 11.06.
Found composition: C, 62.74; H, 6.51; N, 14.59; S, 10.99.
IR (nujol) ν: 1660, 1640, 1575, 1550 cm$^{-1}$.
$^1$H NMR (DMSO-d$_6$) δ$_H$: 12.82 (1H, bs), 8.02 (1H, d), 7.74 (1H, t), 7.49 (1H, d) 7.40 (1H, t), 3.34 (2H, t), 2.64 (2H, t), 2.46 (4H, m), 1.53 (4H, m) and 1.39 (2H, m).
MS (m/z, %): 289 (M$^+$, 1), 178 (3), 111(100), 98 (79).

Example III/4

2-{[2-(2,2,6,6-Tetramethylpiperidin-1-yl)ethyl]thio}quinazolin-4(3H)-one (17d)

Yield: 1.34 g (39%).
Melting point: 221° C.
Calculated composition: C$_{19}$H$_{27}$N$_3$OS: C, 66.05; H, 7.88; N, 12.17; S, 9.26.
Found composition: C, 66.15; H, 7.85; N, 12.29; S, 9.10.
IR (nujol) ν: 1670, 1640, 1575, 1560 cm$^{-1}$.
$^1$H NM (DMSO-d$_6$) δ$_H$: 12.54 (1H, bs), 8.01 (1H, d), 7.74 (1H, t), 7.41 (1H, d), 7.38 (1H, t), 3.07 (2H, m), 2.77 (2H, m), 1.49 (2H, bs), 1.39 (4H, bs) and 1.10 (12H, s).
MS (m/z, %): 345 (M$^+$, <1), 330 (1), 205 (16), 154 (100).

IV. General Procedure According to Reaction Scheme D) [the Structure of the Referred Compounds can be Identified in Reaction Scheme D')]

Compound (19) or (20) (10.0 mmol) dissolved in freshly prepared $CH_2Cl_2$ (10 ml) is added dropwise at 0° C. to the stirred solution of 2-amino-benzonitrile (1.18 g, 10.0 mmol) and $Et_3N$ (1.11 g, 11.0 mmol) dissolved in $CH_2Cl_2$ (20 ml), then the mixed solution is stirred for another hour. The organic phase is washed with 10% aqueous $K_2CO_3$ (15 ml), 5% $H_2SO_4$ (10 ml) in water and brine (15 ml), then the organic phase is separated, dried ($MgSO_4$), filtered and evaporated. The resulting raw amide is then dissolved in a mixture of dioxane (40 ml) and water (40 ml). The mixture is heated to boiling, $NaBO_3 \times 4H_2O$ (4.6 g, 30.0 mmol) is added in small portions under 2 hours, then the reaction mixture is refluxed until all the amide is reacted (5 hours). After cooling the solvents are evaporated under reduced pressure, the residue is dissolved in $CHCl_3$ (20 ml), then washed with brine (10 ml). The organic phase is separated, dried ($MgSo_4$), filtered, evaporated, then the sediment is purified by flash column chromatography ($CHCl_3/Et_2O$).

Example IV/1

2-(1-Oxyl-2,2,5,5-tetramethyl-2,5-dihydro-1H-pyrrol-3-yl)quinazolin-4(3H)-one (21)

Yield: 1.22 g (43%) (yellow substance).
Melting point: 224-226° C.
Calculated composition: $C_{16}H_{18}N_3O_2$: C, 67.57; H, 6.38; N, 14.78.
Found composition: C, 67.41; H, 6.51; N, 14.66.
IR (nujol) ν: 1650, 1600, 1570 $cm^{-1}$.
MS (m/z, %): 284 ($M^+$, 6), 270 (15), 254 (18), 41 (100).

Example IV/2

2-(1-Oxyl-2,2,6,6-tetramethyl-1,2,3,6-tetrahydropyridin-4-yl)quinazolin-4(3H)-one (23)

Yield: 1.04 g (35%) (orange colour).
Melting point: 226-228° C.
Calculated composition: $C_{17}H_{20}N_3O_2$: C, 68.42; H, 6.76; N, 14.09.
Found composition: C, 68.41; H, 6.83; N, 13.94.
IR (nujol) ν: 1670, 1600, 1580 $cm^{-1}$.
MS (m/z, %): 298 ($M^+$, 10), 160 (23), 138 (48), 122 (100).

V. General Synthetic Procedure for Reducing N-oxyl Radical to a Secondary Amine

Iron powder (1.40 g, 25 mmol) is added to the solution of the compound of general formula (I) carrying N-oxyl group in position of Q (5.0 mmol) in glacial acetic acid (8 ml), and the mixture is heated to 70° C., until the reaction begins. The mixture is stirred for an hour, then diluted with water (20 ml), the solution is decanted from the remaining iron powder, the decanted aqueous solution is alkalified with solid $K_2CO_3$. The mixture was extracted with $CHCl_3$ (3×15 mL), dried ($MgSO_4$), filtered, evaporated and after chromatographic purification ($CHCl_3/MeOH$) the resulting amide is obtained as a white or off-white solid material.

Example V/1

3-[(2,2,5,5-Tetramethyl-2,5-dihydro-1H-pyrrol-3-yl)methyl]-2-methylquinazolin-4(3H)-one (9)

Yield: 623 mg (42%).
Melting point: 95-97° C.
Calculated composition: $C_{18}H_{23}N_3O$: C, 72.68; H, 7.80; N, 14.14.
Found composition: C, 72.57; H, 7.82; N, 14.21.
IR (nujol) ν: 3260, 1670, 1630, 1570, 1560 $cm^{-1}$.
$^1$H NMR (DMSO-$d_6$) $\delta_H$: 8.11 (1H, d), 7.90 (1H, t), 7.82 (1H, d), 7.61 (1H, t), 5.79 (1H, s), 5.11 (2H, s), 2.62 (3H, s), 1.29 (6H, s) and 1.18 (6H, s). MS (m/z, %): 297 ($M^+$, 1), 282 (26), 160 (3), 122 (100).

Example V/2

2-{[(2,2,5,5-Tetramethyl-2,5-dihydro-1H-pyrrol-3-yl)methyl]thio}quinazolin-4(3H)-one (13)

Yield: 582 mg (370%).
Melting point: 150-151° C.
Calculated composition: $C_{17}H_{21}N_3OS$: C, 64.73; H, 6.72; N, 13.33; S, 10.15.
Found composition: C, 64.76; H, 6.63; N, 13.23; S, 10.02.
IR (nujol) ν: 3250, 1675, 1605, 1585, 1560 $cm^{-1}$.
$^1$H NMR ($CDCl_3$) $\delta_H$: 8.16 (1H, d), 7.65 (1H t), 7.52 (1H, d), 7.33 (1H, t), 5.60 (1H, s), 3.91 (2H, s), 1.29 (6H, s) and 1.15 (6H, s). MS (m/z, %): 315 ($M^+$, 1), 300 (26), 191 (14), 122 (100).

Example V/3

2-{[(2,2,6,6-Tetramethyl-1,2,3,6-tetrahydropyridin-4-yl)methyl]thio}quinolin-4(3H)-one (15)

Yield: 789 mg (48%).
Melting point: 180-182° C.
Calculated composition: $C_{18}H_{23}N_3OS$: C, 65.62; H, 7.04; N, 12.76; S, 9.71.
Found composition: C, 65.72; H, 7.03; N, 12.59; S, 9.81.
IR (nujol) ν: 3260, 1670, 1610, 1585, 1570 $cm^{-1}$.
$^1$H NMR ($CDCl_3$) $\delta_H$: 8.21 (1H, dd), 7.70 (1H, td), 7.56 (1H, d), 7.38 (1H, t), 5.74 (1H, s), 3.96 (2H, s), 2.03 (2 s), 1.21 (6H, s) and 1.19 (6H, s). MS (m/z, %): 329 ($M^+$, 2), 314(23), 136(100), 121 (92).

Example V/4

2-(2,2,5,5-Tetramethyl-2,5 dihydro-1H-pyrrol-3-yl) quinazolin-4(3H)-one (22)

Yield: 914 mg (68%).
Melting point: 254-256° C.
Calculated composition: $C_{16}H_{19}N_3O$: C, 71.33; H, 7.11; N, 15.61.
Found composition: C, 71.38; H, 7.06; N, 15.60.
IR (nujol) ν: 3240, 1655, 1600, 1570 $cm^{-1}$.
$^1$H NMR (DMSO-$d_6$) $\delta_H$: 12.01 (1H, bs), 8.10 (1H, dd), 7.79 (1H, td), 7.62 (1H, d), 7.49 (1H, td), 6.96 (1H, s), 1.51 (6H, s) and 1.24 (6H, s). MS (m/z, %): 269 ($M^+$, 1), 254 (24), 137 (40), 108 (100).

Example V/5

2-(2,2,6,6-Tetramethyl-1,2,3,6-tetrahydropyridin-4-yl)quinazolin-4(3H)-one (24)

Yield: 816 mg (55%).
Melting point: 265-268° C.
Calculated composition: $C_{17}H_{21}N_3O$: C 72;04; H, 7.47; N, 14.84.
Found composition: C, 72.21; H, 7.53; N, 14.64.
IR (nujol) ν: 3260, 1670, 1600, 1580 $cm^{-1}$.
$^1$H NMR (DMSO-$d_6$) $\delta_H$: 12.01 (1H, bs), 8.10 (1H, d), 7.78 (1H, t), 7.64 (1H, d), 7.47 (1H, t), 6.89 (1H, s), 2.35 (2H, s), 1.23 (6H, s) and 1.13 (6H, s). MS (m/z, %): 283 ($M^+$, 8), 268 (75), 138 (52), 122 (100).

Pharmacological Studies

The protecting effect of 4-quinazolinone derivatives against cell death caused by hydrogen peroxide in WRL-68 human liver cell line.

Cell Culture

The human WRL-68 cell line was obtained from American Type Culture Collection (Rockville, Md.). The one layer thick cell lines were cultured in Dulbecco's modified. Eagle medium containing 1% antibiotic-antimycotic solution and 10% fetal calf serum under humid 37° C. air containing 5% $CO_2$. The cells were separated every three days.

The Detection of Cell Survival

The cells were transformed to a 96-well plate with $2.5 \times 10^4$ cells/well initial concentration and were cultured overnight in humid 37° C. air containing 5% $CO_2$. The following day 0.3 mM hydrogen peroxide was added to the medium either by itself or in the presence of one of the protecting agents. Three hours later the medium was removed and 0.5% water-soluble mitochondria stain, 3-(4,5-dimethylthiazol-2-yl)-2;5-diphenyl-tetrazolium bromide ($MTT^+$) was added to the cells. The incubation was carried on for another three hours, the medium was removed and the metabolically reduced insoluble blue formasan dye was redissolved in acidic isopropanol. The optical density was determined at 550 nm by Anthos Labtech 2010 ELISA Reader (Wien, Austria). In every experiment at least 6 parallel samples were treated and the experiments were repeated three times. Table 1 presents the concentrations (given in μM) where the hydrogen peroxide induced cell death was inhibited by 50%.

The In Vitro Inhibitory Effect of 4-quinazolinone Derivatives on PARP Enzyme

The poly(ADP-ribose) polymerase enzyme was isolated from rat liver as described earlier [22,23]. The putative inhibitory effect of 4-quinazolinone derivatives was examined in this experiment. The activity of the PARP enzyme was determined in 130 μl solution containing 100 mM Tris-HCl buffer (pH 8.0), 10 mM $MgCl_2$, 10% glycerol, 1.5 mM DTT, 1 mM [Adenin-2,8-$^3$H]-$NAD^+$ (4,500 cpm/nmol), 10 μg activated DNA and 10 μg histone. With or without the presence of 4-quinazolinone derivatives, the samples were incubated for 15 minutes, then the reactions were brought to stop by the addition of 8% trichloroacetic acid. After the addition of 0.5 mg albumin the samples were allowed to precipitate for 20 minutes on ice, then the insoluble substances were filtered on a glass filter, collected and washed five times with 5% perchloric acid. The protein-bound radioactivity was measured by LS-200 Beckman scintillation counter, the data is presented in μM in Table 2.

TABLE 1

The inhibitory effect of the 4-quinazolinone derivatives (H-2641, 1-24) against hydrogen peroxide induced cell death in WRL-68 human liver cell line.

| | Substance | | | | | | | |
|---|---|---|---|---|---|---|---|---|
| | H-2641 | 1 | 2 | 3 | 4 | 5 | 8 | 9 |
| $IC_{50}$ (μM) | >100 | 9 | 4 | 70 | >100 | >100 | >100 | 10 |
| Maximum protection (%) | 0 | 50 | 54 | 52 | 0 | 0 | 0 | 15 |

| | Substance | | | | | | | |
|---|---|---|---|---|---|---|---|---|
| | 15 | 17a | 17b | 17c | 17d | 21 | 23 | 24 |
| $IC_{50}$ (μM) | 10 | 0.15 | 4.8 | 0.8 | 0.1 | >100 | 13 | 12 |
| Maximum protection (%) | 61 | 68 | 65 | 62 | 69.6 | 0 | 50 | 50 |

TABLE 2

The in vitro inhibitory effect of the substances 17a-d on PARP enzyme

| | Substances | | | |
|---|---|---|---|---|
| | 17a | 17b | 17c | 17d |
| $IC_{50}$ (μM) | 2 | 6 | 2.6 | 1.6 |

In summary, a series of 4(3H)-quinazolinone derivatives were synthesised by alkylating the original cyclic compounds and by nitrile acylation of antranilic acid, which was followed by the closure of the quinazoline ring. 4-(3H)-quinazolinone derivatives containing S-ethyl sidechains substituted with tertiary amines on the carbon of position 2 proved to be the most effective PARP inhibitors among the synthesised and examined compounds. The effect of nitroxide or amino precursor forms was smaller than that of the tertiary amines, but similar to each other, nevertheless having free radical scavenger ability they might be favourable according to previous results.[9,10,21]

These data show that the compounds of the present invention significantly decrease the effects of oxidative stress and inhibit poly(ADP-ribose) polymerase. The protecting effect of the above mentioned compounds mainly concern their effect on poly(ADP-ribose)-polymerase (PARP) inhibition, thus having a protecting role in every kind of pathological processes, where the protecting-effect of PARP inhibition has a great importance.

Consequently, the compounds of the present invention greatly improve the status of the multiple organ failure syndrome present in sepsis (and its most severe form, septic shock) or in other diseases. Furthermore, they could be used in the treatment of renal failure, hepatic failure, neurodegenerative and inflammatory diseases, and diseases related to ischemia and reperfusion.

Thus, the compounds of the present invention decrease the severity of infarction, type 2 diabetes and insulin resistance as well as the metabolic X syndrome, the rheumatoid arthritis and also decrease the tumour formation in chronic inflammations.

REFERENCES

1. Szabó, Cs. (Ed.) Cell Death, CRC Press, Boca Raton, 2000.
2. de Murcia, G. (Ed) From DNA Damage and Stress Signalling to Cell Death—Poly ADP-Ribosylating Reactions, Oxford University Press, Oxford, 2000.
3. Halmosi, R.; Berente, Z.; Ösz, E.; Tóth, K; Literati-Nagy, P.; Sümegi, B. Mol. Pharmacol. 2001, 59, 1497.
4. Steinhagen, H.; Gerisch, M.; Mittendorf, J.; Schlemmer, K-H.; Albrecht, B. Bioorg. Med. Chem. Lett. 2002, 12, 3187.
5. Li, H-J; Zhang, J. IDrugs 2001, 4, 804.
6. Griffin, J.; Srinivasan, S.; Bowman, K.; Kalvert, H. A.; Curtin, N. J.; Newel, D. R; Pemberton, L. C.; Golding, B. T. J. Med. Chem. 1998, 41, 5247.
7. Tentori, L.; Leonetti, C.; Scarsella, M; d'Amati, G.; Portarena, I.; Zupi, G.; Bonmassar, E.; Graziani, G. Blood 2002, 99, 2241.
8. Hankovszky, H. O.; Hideg, K.; Bódi, I.; Frank L. J. Med. Chem. 1986, 29, 1138.
9. Twomey, P.; Taira, J.; DeGraff, W.; Mitchell, J. B.; Russo, A.; Krishna, M. C.; Hankovszky, H. O.; Frank, L.; Hideg, K. Free Rad. Biol. & Med. 1997, 22, 909.

10. Krishna M. C.; Degraff, W.; Hankovszky, H. O.; Sár, P. C.; Kálai, T.; Jekõ, J.; Russo, A; Mitchell, J. B.; Hideg, K. J. Med. Chem. 1998, 41, 3477.
11. Szabados, E.; Fischer, G. M., Tóth, K; Csete, B.; Németi, B.; Trombitás, K; Habon, T.; Endrei D.; Sümegi, B. Free Rad. Biol. & Med. 1999, 26, 309.
12. Shakhadoyatov, K. M; Yangibaev, S.; Yun, L. M.; Kadirov, C. S. Chem. Natl. Comp. 1982, 18, 106.
13. Liu, K C.; Hsu, L. Y. Arch. Pharm. 1985, 318, 502.
14. Hankovszky, H. O.; Hideg, K.; Lex, L.; Kulcsár, G. Synthesis 1980, 914.
15. Sár, P. C.; Kálai, T.; Bárácz, M. N.; Jerkovich, Gy.; Hideg, K Synth. Commun. 1995, 25, 2929.
16. Hideg, K., Csekõ, J.; Hankovszky, H. O.; Sohár, P. Can. J. Chem. 1986, 64, 1482.
17. Robertson, J.; Biel, J. H.; DiPerro, F. J. Med. Chem. 1963, 6, 381.
18. Huber, L; Szabó, A; Fülöp, F.; Bernáth G.; Sohár, P. Tetrahedron 1992, 48, 4949.
19. Rozantsev E. G. Free Nitroxyl Radicals, Plenum Press, New York, 1970.
20. Baudoin, B.; Ribeill, B.; Vicker, N. Synth. Commun. 1993, 23, 2833.
21. Samuni, A; Goldstein, S.; Russo, A.; Mitchell, J. B.; Krishna, M. C.; Neta, P. J. Am. Chem. Soc. 2002, 124, 8719.
22. Shah, G. M.; Poirier, D; Duchaine, C.; Brochu, G.; Desnoyers, S; Lagueux, J.; Verreult, A.; Hoflack, J. C.; Kirkland, J. B.; Poirier, G. G. Anal. Biochem. 1995, 227, 1.
23. Szabados, E.; Literáti-Nagy, P.; Farkas, B.; Sümegi, B. Biochem. Pharmacol. 2000, 59, 937.
24. Skalitzky, D. J.; Marakovits, J. T.; Maegley, K. A.; Ekker, A.; Yu, X-H.; Hostomsky, Z.; Webber, S. E.; Eastman, B. W.; Almassy, R.; Li, J.; Cuirtin, N. J.; Newell, D. R.; Calvert, A. H.; Griffin, R. J.; Golding, B. T. J. Med. Chem, 2003, 46, 210-213.

Figure 1:
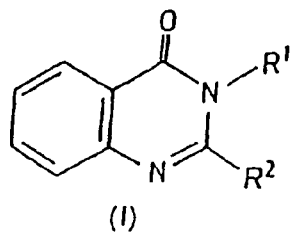
FIG. 1 illustrates a compound of general formula (I)
Figure 2:
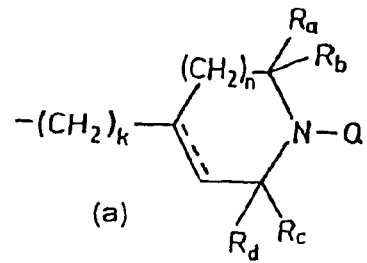
FIG. 2 illustrates a compound of general formula (a)
Figure 3:
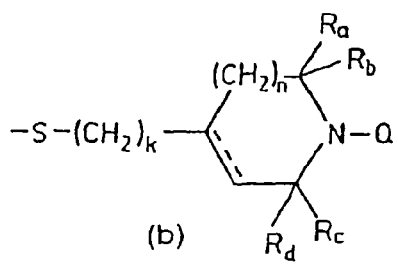
FIG. 3 illustrates a compound of general formula (b)
Figure 4:
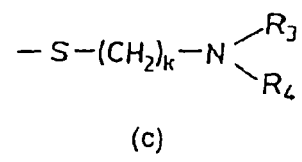
FIG. 4 illustrates a compound of general formula (c)
Figure 5:
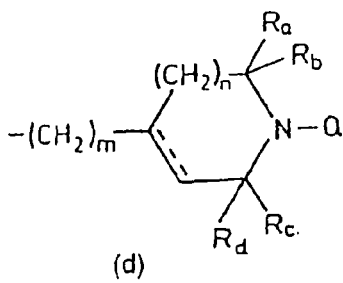
FIG. 5 illustrates a compound of general formula (d)
Figure 6:
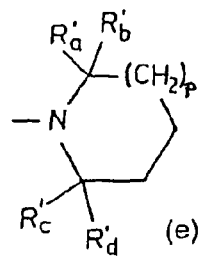
FIG. 6 illustrates a compound of general formula (e)
Figure 7:
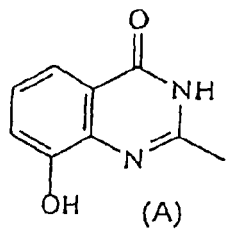
FIG. 7 illustrates a compound of general formula (A)
Figure 8:
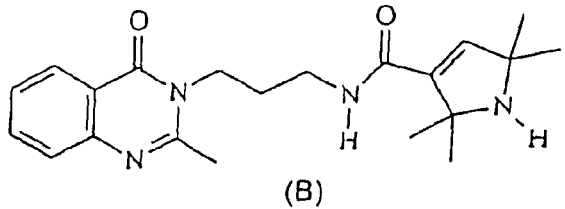
FIG. 8 illustrates a compound of general formula (B)
Figure 9:
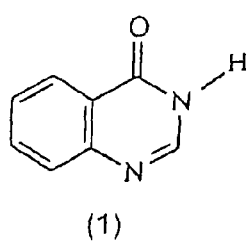
FIG. 9 illustrates a compound of general formula (1)
Figure 10:
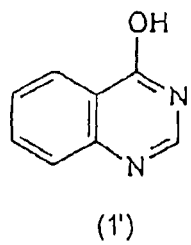
FIG. 10 illustrates a compound of general formula (1')
Figure 11:
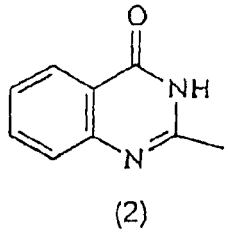
FIG. 11 illustrates a compound of general formula (2)
Figure 12:
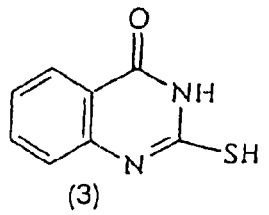
FIG. 12 illustrates a compound of general formula (3)
Figure 13:
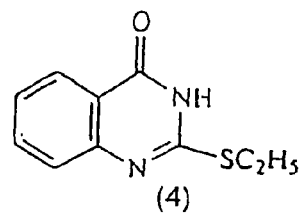
FIG. 13 illustrates a compound of general formula (4)
Figure 14:
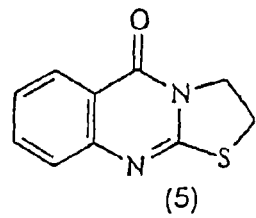
FIG. 14 illustrates a compound of general formula (5)
Figure 19:
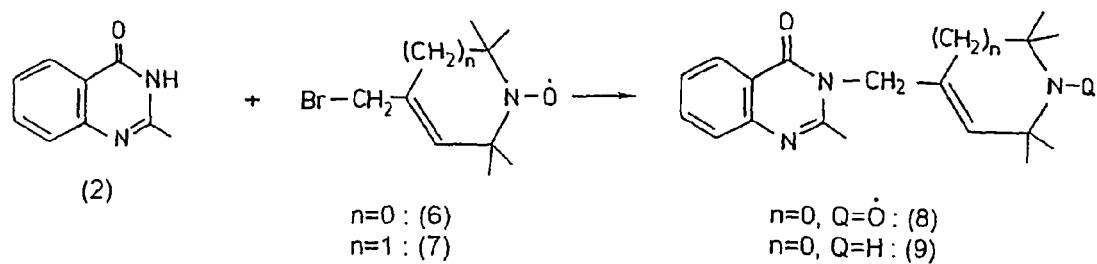
FIG. 19 illustrates Reaction Scheme A'.
Figure 20:
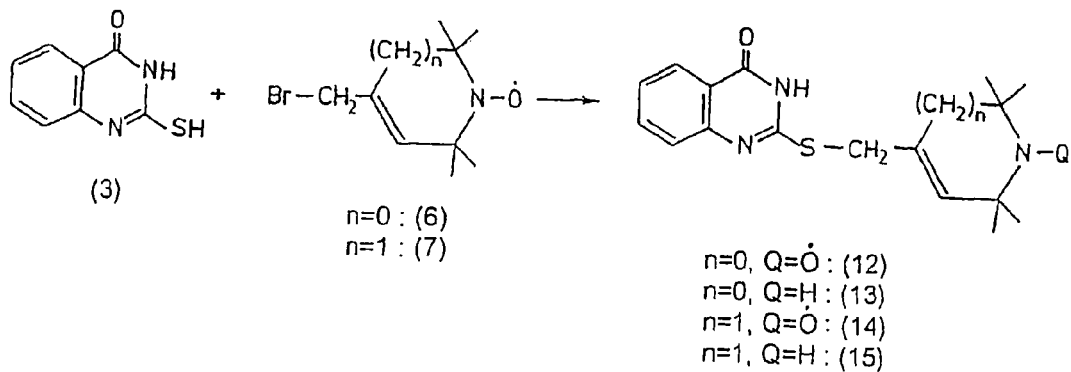
FIG. 20 illustrates Reaction Scheme B'.
Figure 21:
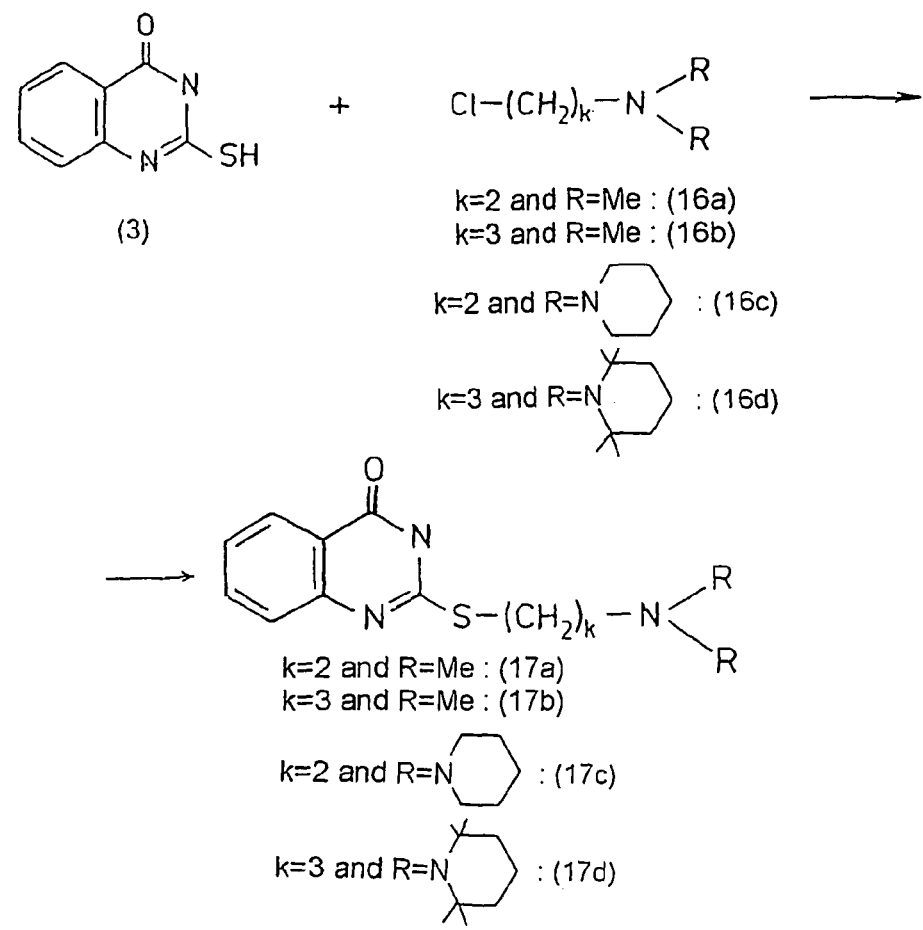
FIG. 21 illustrates Reaction Scheme C'.
Figure 22:
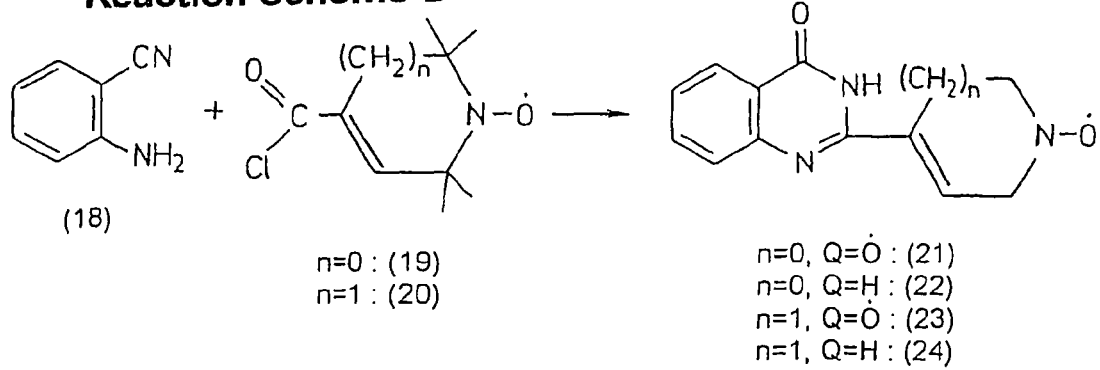
FIG. 22 illustrates Reaction Scheme D'.

| Summary of drawings | |
|---|---|
| FIG. 1 | General formula (I) |
| FIG. 2 | General formula (a) |
| FIG. 3 | General formula (b) |
| FIG. 4 | General formula (c) |
| FIG. 5 | General formula (d) |
| FIG. 6 | General formula (e) |
| FIG. 7 | General formula (A) |
| FIG. 8 | General formula (B) |
| FIG. 9 | General formula (1) |
| FIG. 10 | General formula (1') |
| FIG. 11 | General formula (2) |
| FIG. 12 | General formula (3) |
| FIG. 13 | General formula (4) |
| FIG. 14 | General formula (5) |
| FIG. 15 | Reaction Scheme A |
| FIG. 16 | Reaction Scheme B |
| FIG. 17 | Reaction Scheme C |
| FIG. 18 | Reaction Scheme D |
| FIG. 19 | Reaction Scheme A' |
| FIG. 20 | Reaction Scheme B' |
| FIG. 21 | Reaction Scheme C' |
| FIG. 22 | Reaction Scheme D' |

The invention claimed is:

1. Compounds of general formula (I) and their pharmaceutically acceptable salts thereof

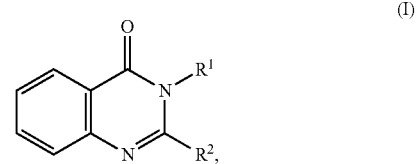

wherein $R^1$ stands for hydrogen or a group of general formula (a)

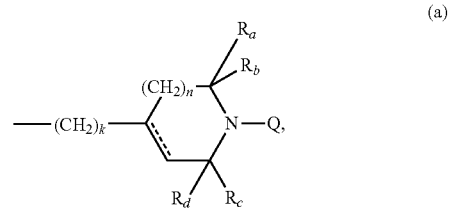

and k is 1, 2, 3, or 4, n is 0 or 1,

Q stands for oxyl group (O.) or hydrogen,

Ra and Rc independently from each other stand for hydrogen or $C_{1-6}$ alkyl group, Rb and Rd independently from each other stand for $C_{1-6}$ alkyl group and the broken line stands for an optional valence bond;

$R^2$ stands for a) hydrogen or $C_{1-6}$ alkyl group, if $R^1$ is other than hydrogen, and b) if $R^1$ is a hydrogen, then $R^2$ stands for (i) a group of general formula (b)

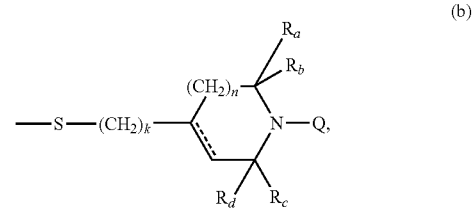

wherein the meanings of k, n, Q, Ra, Rb, Rc, Rd and the broken line are as given above, or (ii) a group of general formula (c)

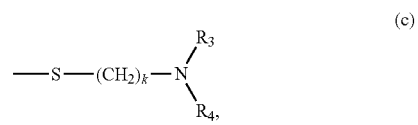

wherein k is 1, 2, or 3; and R3 and R4 together with the attached nitrogen form a group of general formula (e)

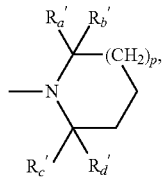

wherein p is 0 or 1 and R'a, R'b, R'c and R'd independently from each other stand for hydrogen or $C_{1-6}$ alkyl group, or (iii) a group of general formula (d)

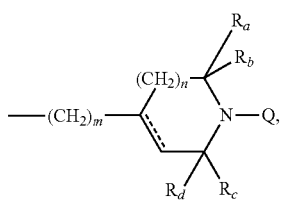

wherein the meanings of n, Q, Ra, Rb, Rc, Rd, and the broken line are as given above and m is 0, 1, 2 or 3.

2. The compounds of general formula (I) according to claim 1, wherein $R^1$ stands for a group of general formula (a), k=1, n=0, Q=hydrogen, Ra, Rb, Rc and Rd each stand for $C_{1-3}$ alkyl group, and the broken line stands for a valence bond.

3. The compounds of general formula (I) according to claim 1, wherein $R^2$ stands for a group of general formula (b), k=1, n=0 or 1, Ra, Rb, Rc and Rd each stand for $C_{1-3}$ alkyl group, and the broken line stands for a valence bond.

4. The compounds of general formula (I) according to claim 1, wherein $R^2$ stands for a group of general formula (b), k=1, n=1, Q=hydrogen, Ra, Rb, Rc and Rd each stand for $C_{1-3}$ alkyl group, and the broken line stands for a valence bond.

5. The compounds of general formula (I) according to claim 1, wherein $R^2$ stands for a group of general formula (c), k=2 or 3, $R^3$ and $R^4$ together stand for a group with structural formula (e), p=1 and R'a, R'b, R'c and R'd each stand for a hydrogen atom.

6. The compounds of general formula (I) according to claim 1, wherein $R^2$ stands for a group of general formula (c), k=2 or 3, $R^3$ and $R^4$ together stand for a group with structural formula (e), p=1 and R'a, R'b, R'c and R'd each stand for $C_{1-3}$ alkyl group.

7. The compounds of general formula (I) according to claim 1, wherein $R^2$ stands for a group of general formula (d), m=0, n=0 or 1, Ra, Rb, Rc and Rd each stand for $C_{1-3}$ alkyl group, and the broken line stands for a valence bond.

8. The compounds of general formula (I) according to claim 1, wherein $R^2$ stands for a group of general formula (d), m=0, n=1, Ra, Rb, Rc and Rd each stand for $C_{1-3}$ alkyl group, and the broken line stands for a valence bond.

9. A pharmaceutical composition comprising one or more compounds of claim 1, as active ingredients together with pharmaceutically acceptable auxiliary ingredients.

* * * * *